(12) United States Patent
Dobai et al.

(10) Patent No.: US 10,720,237 B2
(45) Date of Patent: Jul. 21, 2020

(54) METHOD OF AND APPARATUS FOR OPERATING A DEVICE BY MEMBERS OF A GROUP

(71) Applicant: KONINKLIJKE PHILIPS N.V., Eindhoven (NL)

(72) Inventors: Iulia Dobai, Eindhoven (NL); Njin-Zu Chen, Eindhoven (NL); Marleen Johanna Jacoba Van Leengoed, Waarle (NL)

(73) Assignee: Koninklijke Philips N.V., Eindhoven (NL)

( * ) Notice: Subject to any disclaimer, the term of this patent is extended or adjusted under 35 U.S.C. 154(b) by 92 days.

(21) Appl. No.: 15/567,729

(22) PCT Filed: Apr. 15, 2016

(86) PCT No.: PCT/EP2016/058430
§ 371 (c)(1),
(2) Date: Oct. 19, 2017

(87) PCT Pub. No.: WO2016/173865
PCT Pub. Date: Nov. 3, 2016

(65) Prior Publication Data
US 2018/0130556 A1 May 10, 2018

(30) Foreign Application Priority Data
Apr. 29, 2015 (EP) ..................................... 15165570

(51) Int. Cl.
*G16H 40/60* (2018.01)
*G06Q 10/10* (2012.01)
(Continued)

(52) U.S. Cl.
CPC ............. *G16H 40/60* (2018.01); *G06Q 10/10* (2013.01); *G06Q 30/02* (2013.01); *G06Q 50/22* (2013.01); *G16H 40/40* (2018.01); *G16H 80/00* (2018.01)

(58) Field of Classification Search
None
See application file for complete search history.

(56) References Cited

U.S. PATENT DOCUMENTS 5,941,956 A * 8/1999 Shirakihara ............. H04L 29/06
709/200
6,402,737 B1 6/2002 Tajima et al.
(Continued)

FOREIGN PATENT DOCUMENTS

CN 103605426 A 2/2014
EP 0919906 A2 6/1999

OTHER PUBLICATIONS

Bigdelou et al., "An Adpative Solution for Intra-Operative Gesture-based Human-Machine Interaction", ACM 978-1-4503-1048-2, 2012.*
(Continued)

*Primary Examiner* — Piotr Poltorak

(57) ABSTRACT

A method and apparatus for operating a device by controlling the device based on input received from group members, uses a sensor for monitoring each group member for detecting an instruction provided by a group member. The instruction includes a visual or audible instruction. Upon detecting, a controller associates a control command with the instruction. The controller provides the control command to the device. For establishing the group, an authentication is performed for adding a user as a group member. For identifying the control command, the detected instruction is associated with the instructing group member, where the member profile is accessed from a memory including a set of reference instructions, and the instruction is matched
(Continued)

with a reference instruction selected from the set of reference instructions in the profile.

12 Claims, 3 Drawing Sheets

(51) Int. Cl.
  *G06Q 50/22* (2018.01)
  *G16H 80/00* (2018.01)
  *G06Q 30/02* (2012.01)
  *G16H 40/40* (2018.01)

(56) References Cited

U.S. PATENT DOCUMENTS

| | | | | |
|---|---|---|---|---|
| 6,421,453 | B1* | 7/2002 | Kanevsky | G06F 21/316 340/5.2 |
| 7,346,696 | B2* | 3/2008 | Malik | H04L 63/105 707/999.009 |
| 8,015,014 | B2* | 9/2011 | Wang | G10L 15/26 704/275 |
| 9,215,226 | B2* | 12/2015 | Sanso | H04L 63/104 |
| 9,398,937 | B2 | 7/2016 | Guez et al. | |
| 2002/0075334 | A1* | 6/2002 | Yfantis | G06F 3/017 715/863 |
| 2004/0019489 | A1* | 1/2004 | Funk | H04L 12/2803 704/275 |
| 2004/0123091 | A1* | 6/2004 | Das | H04L 29/06 713/2 |
| 2004/0193413 | A1* | 9/2004 | Wilson | G06F 3/017 704/243 |
| 2007/0283296 | A1* | 12/2007 | Nilsson | G06F 3/017 715/863 |
| 2008/0004951 | A1 | 1/2008 | Huang et al. | |
| 2008/0052203 | A1* | 2/2008 | Beyer | G06Q 10/087 705/28 |
| 2008/0256494 | A1* | 10/2008 | Greenfield | G06F 3/0304 715/863 |
| 2011/0037840 | A1* | 2/2011 | Hiltl | A61B 90/35 348/61 |
| 2011/0304541 | A1* | 12/2011 | Dalal | G06F 3/017 345/158 |
| 2011/0319117 | A1* | 12/2011 | Gonsalves | H04L 12/1822 455/519 |
| 2013/0310652 | A1* | 11/2013 | Barsoum | A61B 90/30 600/249 |
| 2014/0049465 | A1* | 2/2014 | Tremaine | G06F 3/017 345/156 |
| 2014/0181238 | A1* | 6/2014 | Sumrall | G06F 21/00 709/216 |
| 2015/0033297 | A1* | 1/2015 | Sanso | H04L 63/104 726/5 |
| 2016/0091875 | A1* | 3/2016 | Lloyd | G05B 15/02 700/79 |
| 2016/0094874 | A1* | 3/2016 | Venkataraman | H04N 21/441 725/10 |
| 2016/0303739 | A1* | 10/2016 | Apkarian | B25J 3/04 |
| 2016/0359874 | A1* | 12/2016 | Black | H04L 63/1416 |
| 2017/0186292 | A1* | 6/2017 | Friedman | G08B 13/196 |
| 2018/0081447 | A1* | 3/2018 | Gummadi | G06F 3/017 |

OTHER PUBLICATIONS

Jacob et al. "Hand-gesture-based sterile interface for the operating room using contextual cues for the navigation of radiological images", J AM Med Inform Assoc, 2013.*
A. Bigdelou et al., "HCI Design in the OR: A Gesturing Case-Study", Computer Aided Medical Procedures, Oct. 1, 2012, p. 16.
H. Mentis et al., "Voice or Gesture in the Operating Room", Human Factors in Computing Systems, ACM, 2 Penn Plaza, Suite 701, New York, NY, 10121-0701 USA, Apr. 18, 2015, pp. 773-780.
T. R. Hansen et al., "ActiveTheatre—A Collaborative, Event-Based Capture and Access System for the Operating Theatre", Aug. 19, 2005, UBICOMP 2005: Ubiquitous Computing; [Lecture Notes in Computer Science;;LNCS], Springer-Verlag, Berlin/Heidelberg, pp. 375-392.

* cited by examiner

METHOD OF AND APPARATUS FOR OPERATING A DEVICE BY MEMBERS OF A GROUP

CROSS-REFERENCE TO PRIOR APPLICATIONS

This application is the U.S. National Phase application under 35 U.S.C. § 371 of International Application No. PCT/EP2016058430, filed on 15 Apr. 2016, which claims the benefit of European Patent Application No. 15165570.1, filed on 29 Apr. 2015. These applications are hereby incorporated by reference herein.

TECHNICAL FIELD OF THE INVENTION

The present invention relates generally to a method of operating a device by controlling the device based on input received from one or more group members of a group, the method comprising the steps of: monitoring, using a sensor unit, each group member for detecting at least one instruction provided by an instructing group member of said one or more group members, said instruction including at least one of a visual or audible instruction; identifying by a control unit, upon detecting of the instruction, a control command associated with the instruction; and providing, by said control unit, the control command to the device for controlling the device. The invention further relates to an apparatus for performing such a method, and to a computer program product.

BACKGROUND OF THE INVENTION

Methods and systems for operating devices by means of gestures or spoken voice are available in different variants and fields of application. Early implementations of such systems simply relied on the detection of motion by a motion sensor to operate devices such as lights, cameras or alarm systems. More sophisticated implementations are able to detect specific motion patterns, to enable a user to target operation of the device by specific gestures or to make operation of the device less sensible to just any kind of motion in front of the sensor.

Face detection and face recognition in images and videos is becoming a standard feature/capability of many systems (for example Google's Picasa or Windows Live). Other means of tracking a person's presence and location in a closed environment exist and are being used, for example the use of RFID based solutions through which persons wearing RFID tags may be continuously tracked with long range detection and triangulation techniques.

European patent no. EP0919906 discloses a control method and system that allow input to be provided in the form of gestures for controlling devices. The method includes an operator selection section that recognizes attributes of a person making a gesture. The additional information on the operators attributes are used to prioritize some operators over others.

The published US patent application US2008/0004951 discloses an architecture for presenting advertisements in real time in retail establishments. A sensor component includes sensors for collecting information about one or more customers as they move through the store. The sensors can include capability for image processing, audio processing, light sensing, velocity sensing, direction sensing, proximity sensing, face recognition, pose recognition, transaction recognition, and biometric sensing, for example. A customer component analyzes the information and generates a profile about the customer. Advertisements are selected for presentation that target the customers as they walk in proximity of a presentation system of the store. An advertisement component facilitates dynamic presentation of a targeted advertisement to the individual as a function of the profile. The customer component can infer information during analysis using machine learning and reasoning.

In medical settings such as in an operation room of a hospital, a group of persons may be assigned to perform a specific team task being supported by medical equipment. For example, in a surgical theatre a number of people (surgical staff) work together to jointly perform a surgery. The surgery will usually be conducted by a surgeon who is also the leading responsible team member. The surgeon relies on the anesthetist for performing anesthesia, and on other medical staff members for performing other tasks. Together, the surgical team members control a number of medical systems. These systems are generally operated through physical buttons or switches. Generally the main surgeon(s) cannot operate the medical system himself (either because their hands are busy with the patient or their hands are sterile while parts they need to touch are not) and request other medical staff to operate the devices.

In "HCI Design in the OR: A Gesturing Case-Study", by Ali Bigdelou et al., Computer Aided Medical Procedures, Technische Universität München, and Klinikum München-Posing, October 2012, it is disclosed a computerized system for controlling medical equipment in an operating room by means of a gesture-based interface.

Document "Voice or Gesture in the Operating Room", by Helena M. Mentis et al., Human Factors in Computing Systems, ACM, 2 Penn Plaza, Suite 701 New York N.Y. 10121-0701 USA, 18 Apr. 2015, pp. 773-778, presents another of such systems that allows for both gestural or voice control at the choice of the surgeon.

SUMMARY OF THE INVENTION

The objects of the present invention are solved by the independent claims. Advantageous embodiments are defined in the dependent claims.

It is an object of the present invention to provide an equipment control method based on visual or audible instructions that may be implemented to be operated by a team of operators that jointly perform a certain task, such as a surgical team.

The invention achieves these and other objects in that it provides for a method of operating a device by controlling the device based on input received from one or more group members of a group. The method comprises monitoring, using a sensor unit, each group member for detecting at least one instruction provided by an instructing group member of said one or more group members. This instruction may include at least one of a visual or audible instruction. The method further identifies, by a control unit upon detecting of the instruction, a control command for controlling the device, the control command being associated with the instruction. The control unit provides the control command to the device. For establishing the group the method further comprises a step of performing, by user input means for interacting with a user, an identity authentication of a user for adding said user as a group member. For said identifying of the control command, the method comprises: associating by the control unit the detected instruction with the instructing group member among the group members, accessing a member profile data of the instructing group member from a memory unit, the member profile data of the instructing group member comprising a set of reference instructions, and matching the detected instruction with a given reference instruction selected from the set of reference instructions in the member profile data of the instructing group member for identifying the control command.

As may be appreciated, the use of gesture based equipment control has the potential to enable a surgeon to have direct control over medical systems in situations where this would not be possible in a conventional setting. This may be preferred for example when performing certain actions, such as (time) critical actions, since it reduces the response time for performing the action and may reduce the risk of error (recognizing that spoken communication between team members may be prone to error, especially in the presence of background sounds). The invention is based on the insight that conventional gesture based control methods are not fit to be implemented in critical medical settings such as a surgery. These conventional methods often lack sufficient reliability. Moreover, these methods do not take roles and responsibilities of the team members into account. For example, in a surgical theatre the roles and responsibilities of the members of the surgical staff are clearly defined, e.g. to prevent conflicting actions and optimally apply the skills of the members.

The terms visual instructions and audible instructions, are to be understood as including any instruction that may be detected using sensor units that enable to detect changes over time in a specific area. The instructions include gestures, voice spoken instructions, sound instructions (e.g. clapping of hands), poses taken by a group member (e.g. maintaining a hand temporarily in a fixed position). These instructions could also be combinations of the above, such as the detection of a sound with a corresponding motion of a group member. For example, clapping of hands with the detection of hands of a specific group member moving towards each other, or a voice command including the detection of moving lips. Other examples are a gesture being made including an additional voice command, such as raising both hands in a crossed manner while pronouncing "full stop", or making a lifting motion with one hand while pronouncing the name of a parameter to increase (e.g. lifting a hand while saying "adrenaline" and "slowly").

The method of the present invention performs identity authentication prior to adding group members to the group. The group of persons that can control the device is thereby clearly defined for each group task. For example, each of the persons (users) that participate in performing the group task must first join the group by completing the identity authentication session. Without authentication, a person is ignored by the system performing the method. After authentication, since each group member is monitored by the system, the system will monitor the authenticated group member. In some embodiments, authentication may take place at the start of the group task, e.g. prior to the start of the surgery. In other embodiments, it may also be possible to add group members at any time from the start, e.g. later on during the surgery to allow additional skills to be added to the surgical staff when these are unexpectedly required.

Being aware of the identity of group members by means of the authentication, the invention also takes roles and responsibilities of the group members within the group into account. This is achieved in that, for identifying the control command, the detected instruction is associated by the control unit with the instructing group member among the group members, after which it is matched with reference instructions in a member profile of the instructing group member. The member profile data of the instructing group member is thereto accessed by the control unit from a memory unit.

This has several benefits. As explained, by verifying the instruction against a member profile, no group member may provide an instruction that he or she is not authorized to provide. For example, in certain embodiments, the identification of the control command may further comprise a verification of an authorization status obtained from the member profile data of said instructing group member. Other embodiments may relate the member profile data to a classification, e.g. based on a defined function group that corresponds with the role of the group member in the group. Thereby, authorization status may follow from such a classification.

Moreover, the use of reference instructions may, in certain embodiments, also allow to personalize the gestures and voice commands used by each group member. Even in embodiments that rely on standardized instructions, such as standardized gestures, voice commands, sounds, or poses, the meaning of such instructions may be personalized. This allows to take the roles and responsibilities of group members fully into account.

In some embodiments, the step of monitoring includes continuously tracking of each group member once said respective group member has been authenticated. By continuously tracking of each of the respective group members after identity authentication, it is prevented that errors are made in recognition of group members. Once identity authentication is performed, the presence of each group member in images received from the sensor unit may be continuously tagged, such as to enable association of detected instructions with the instructing group member. Moreover, it may also prevent that instructions provided by group members are missed by the system performing the method.

The availability of detailed information on which team member provided which detected instruction, further allows in some embodiments to automatically keep track electronically of the group task to be performed. All instructions may, for example, be logged in a log file for later evaluation and training purposes.

The method of the invention is not restricted only to the control of a single device, but may be implemented, in accordance with an embodiment, to control a plurality of devices. In accordance with such an embodiment, the control unit may be comprised by a central unit receiving sensor signals from said sensor unit, and the memory unit is accessible by said control unit. The method in accordance with this embodiment may comprise the steps of: identifying, by the control unit, a candidate device for receiving the control command, wherein the candidate device is identified by means of said matching of the detected instruction with the reference instruction in the member profile data of said instructing group member.

In accordance with a further aspect, there is provided an apparatus for controlling operation of a device by controlling the device based on input received from one or more group members of a group, the apparatus comprising: a sensor unit for monitoring each group member for detecting at least one instruction provided by an instructing group member of said one or more group members, said sensor unit being arranged for receiving at least one of visual images or audible signals such as to detect visual or audible instructions; a control unit communicatively connected to said sensor unit for receiving an output signal from said sensor unit, said control unit including a processor for identifying upon detecting of the instruction a control command for controlling the device, the control command being associated with the instruction, wherein the control unit is communicatively connected to the device for providing the control command to the device; user input means for interacting with a user for performing an identity authentication of said user for adding said user as a group member for establishing the group; and a memory unit for storing one or more member profile data of the group members, the member profile data of each group member comprising a set of reference instructions for said group member; wherein the control unit by said processor is further arranged for associating the detected instruction with the instructing group member among the group members, accessing the member profile data of the instructing group member from the memory unit, and matching the detected instruction with a given reference instruction selected from the set of reference instructions in the member profile data of the instructing group member for identifying the control command.

In an embodiment, the user input means may comprises at least one element of a group comprising: a biometrics scanner, including an iris scanner or retina scanner for authenticating the user based on personal eye characteristics, or a fingerprint scanner; a keyboard for entering personal log-on details, a touch sensitive screen, or a camera.

Moreover, in accordance with some embodiments, the sensor unit comprises at least one element of a group comprising an imaging device or imaging arrangement, including one or more cameras for observing a region, an audio sensor device or audio sensor arrangement, including one or more microphones for sensing audio signals.

According to a third aspect, the invention relates to a computer program product downloadable from a communication network and/or stored on a computer-readable and/or microprocessor-executable medium, the product comprising program code instructions for implementing a method for operating a device by controlling the device based on input received from one or more group members of a group in accordance with the first aspect of the invention. Moreover, the invention relates, in accordance with a further aspect, to a data carrier comprising such a computer program product.

BRIEF DESCRIPTION OF DRAWINGS

Herein below, the invention will be described by some specific embodiments thereof, with reference to the enclosed drawings, wherein.

DETAILED DESCRIPTION OF THE EMBODIMENTS

Where in the description, reference is made to 'gestures', it is to be understood that any other type of instruction mentioned anywhere in this document may be substituted therefore, such as voice spoken instructions, sound instructions (e.g. clapping of hands), poses taken by a group member (e.g. maintaining a hand temporarily in a fixed position) or combinations of any such instructions. Moreover, the term identity authentication is to be interpreted as any action or method that allows to reliably establish the identity of a user or person. The desired level of reliability may of course be dependent on the implementation. For some implementations, identification by means of access badge may be sufficient, while for other implementations a fingerprint or retina scan is preferred.

Figure 1:
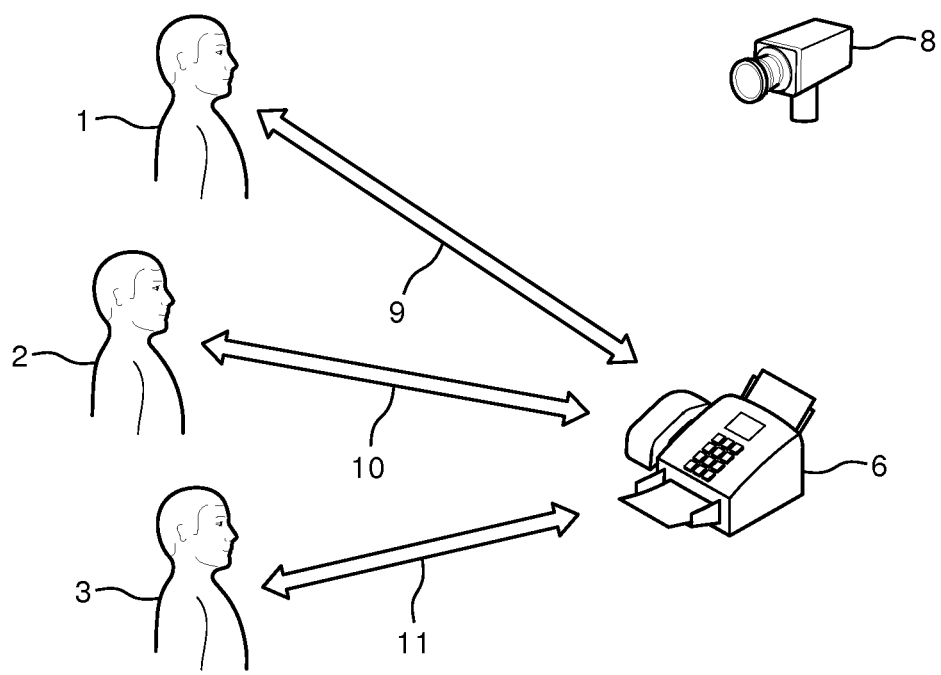
FIG. 1 illustrates a setting of the present invention.

In FIG. 1, a setting wherein the present invention is applied is schematically illustrated. In FIG. 1, a plurality of group members 1, 2 and 3 may operate a device 6 while performing a task. FIG. 1 is merely schematic and illustrates an office environment wherein colleagues 1, 2 and 3 together use a number of devices, such as facsimile device 6. The group members 1, 2 and 3 may have different roles and responsibilities within the group and corresponding therewith, instructions provided by any of the group members 1, 2 or 3 may have different priorities of being followed up by device 6. A tracking system 8 (e.g. one or more cameras) may monitor the region wherein the group members 1, 2 and 3 are working. The tracking system 8 enables to monitor each of the group members 1, 2 and 3 such as to identify gestures or sounds being made by either group member. Each of the group members 1, 2 and 3 may provide input to the device 6 and receive feedback, as is indicated respectively by double arrows 9, 10 and 11. As will be explained further below, tracking system 8 may be communicatively connected with a control unit (not shown) which receives the information on whether or not an instruction has been given by one of the group members 1, 2 or 3.

Prior to being added as a group member, an identity authentication session may be required for either group member 1, 2 or 3 to be added. After performing the authentication, the control unit may access a personal profile or member profile from a member unit. Using the member profile, the dialogues 9, 10 and 11 between either group member 1, 2 or 3 and the device 6 may be personalized. Personalization of the dialogue may comprise each of the group members 1, 2 and 3 using personalized gestures as input to the device 6. In other words, gestures may have different meanings dependent on the group member (1, 2, or 3) that provides the instruction. Moreover, also any feedback from the device 6 to the instructing group member (1-3) in the dialogues 9, 10 and 11 may be personalized. As will be appreciated, personalization may also include that each group member 1, 2 and 3 has its own personalized set of actions for which the group member is authorized. Certain functions of device 6 may for example only be accessed by group member 1, while other functions may be available to all group members.

Figure 2:
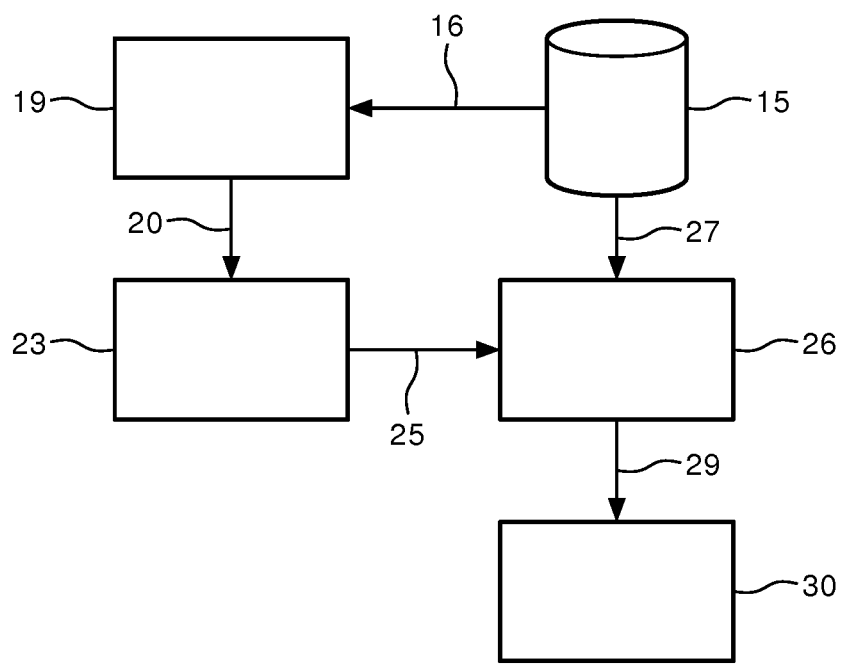
FIG. 2 schematically illustrates the method of the present invention.

The tracking system 8 may be a people tracking system which is based on existing tracking functionality (such as for example face detection and recognition, RFID tagging, etc.). With reference to FIG. 2, each to be tracked person 1, 2 or 3 is first uniquely identified in step 19 during the identity authentication session with a reliable mechanism such as retina scanning, fingerprint recognition, access badge, etc. Please note that such a mechanism may not be used continuously for tracking. Authentication in many cases provides for a momentary identification, and therefore requires additional means to keep track of group members. Thus the combination of a one-time or an intermittently used identification mechanism and a continuous tracking mechanism (step 23) is preferred. The identity authentication session 19 may in some embodiments, as indicated in FIG. 2 by arrow 16, obtain personal information from a member profile stored in a member data collection 15 (e.g. available from a memory unit). Once authentication is completed the person identified will be added as group member. Data which may contain part of the (or even the complete) member profile data available in member data collection 15, may be provided to the system for further use as indicated by arrow 20. Also, alternatively, only a reference to the member profile data in the memory unit may be provided. This may for example enable tagging of persons tracked by the tracking system 8 to enable association of any instructions (see the description of the events below) with the member profile of the person (now group member) that provided the instruction.

During the tracking process 23, each tracked person's interaction with the system (by means of gestures, spoken voice, a pose, or the like) raises an event 25. An event may contain one, or more, or all of an identity, a location, a timestamp and an input instruction (gesture, pose, voice command, etc). The event 25 is made available to a control unit for further processing. The software controlling the control unit takes this event as input to step 26. A second input 27 for the controlling system is obtained from the member data collection 15 with all identities and their roles, permissions and known gestures and personal preferences. Based on the two inputs 25 and 27 the control unit decides in step 26 on the proper action for the equipment 6 to be controlled, and provides adequate feedback to the group member issuing the instruction. This feedback may be personalized since the system knows who issued the command (using input 25) and what his preferences are (based on the member profile data 27 obtained from the member data collection 15). This allows for a highly personalized two-way dialog between each individual and a complex system and in parallel for multiple individuals. Based on the outcome of step 26, a control command 29 is provided to the equipment 6 which leads to the required action to be performed in step 30.

Figure 3:
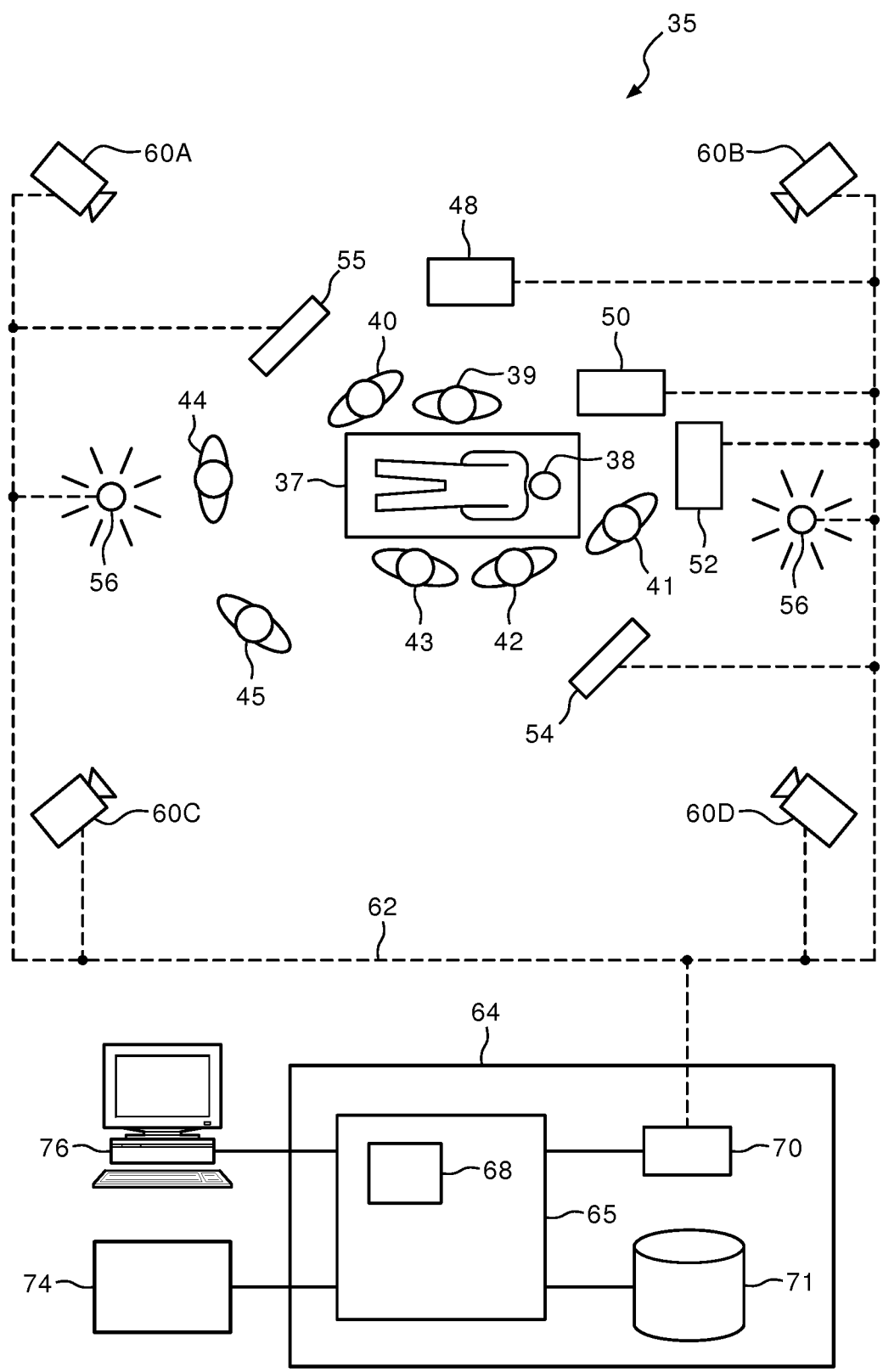
FIG. 3 schematically illustrates a system in accordance with the present invention.

In FIG. 3, a further example of a system 35 in accordance with an embodiment of the present invention is illustrated which relates to a medical setting. In FIG. 3, an operation room including an operation table 37 on which a patient 38 to be operated on are illustrated. Around the table 37, a plurality of surgical staff members 39, 40, 41, 42, 43, 44, 45 are schematically indicated. Each of the surgical staff member 39-45 has different roles and responsibilities within the team. For example, the surgeon 39 may be the head of the team leading the surgery. The surgeon 39 is assisted by an assistant surgeon 42 and a cardiologist 43. An anesthetist 41 performs anesthesia while permanently monitoring the patients 38 vital signs. Further present are operation assistants 40 and 44, and a further medical practitioner 45 on stand-by. Monitor displays 54 and 55 are strategically placed in the operation room and may be used by the surgical staff to provide information or images or the like, to support the surgery. Lighting in the operation room is provided by lighting units 56. Also part of the medical support equipment are devices 48, 50 and 52 performing different functions.

The operation room is equipped with a number of cameras 60A, 60B, 60C, and 60D which together form the tracking system 60. As will be appreciated, although in the example of FIG. 3 four cameras are illustrated, the number of cameras or other sensing units that is required for enabling tracking of the group members 39-45 may be different for each situation. For example, in some embodiments only a single sensing unit or camera may be sufficient while in other embodiments, a number of different rooms that may be interconnected by doors and hallways may be equipped with twenty or thirty cameras which together form the tracking system. Moreover, instead of cameras or in addition thereto, other sensor units may be applied such as microphones, RFID scanners, heat sensors, or any combination of suitable sensors for tracking persons may be part of a tracking system 60.

In the embodiment of FIG. 3, all the devices to be controlled 48, 50, 52, 54, 55 and 56, and the cameras 60A-60D are interconnected by a network (62) which is schematically indicated by dashed lines. The network 62 also connects to a central unit 64. As will be appreciated the network 62 may be a wired network, a wireless network, or a combination of a wired and wireless network for interconnecting with the devices and cameras mentioned. The skilled person will be able to select the most suitable network combination for the situation at hand.

The sensing units 60A-60D (cameras) continuously track the movements poses and any audio signals coming from any of the group members 39-45. Being located on four different sides of the operation room, together the sensing unit 60A-60D will be able to detect any gesture, pose, or audio signal provided by any group member intended as an instruction for the control of any of the devices 48, 50, 52, 54, 55 and 56. The sensor units or cameras 60A-60D may be installed at an elevated position relative to the group members 39-45, or may be placed in a different strategic configuration for enabling effective registration of the instructions provided.

Prior to being tracked by the system with sensor units 60A-60D, each of the surgical staff members 39-45 will have to complete an identity authentication session with the system such as to enable the system to associate these persons with a member profile stored in memory unit 71 of the central unit 64. The authentication session may be performed in various ways, as already indicated above. In the embodiment of FIG. 3, group members may log into the system using a regular log-in procedure performed at an input terminal 76. Alternatively, or in addition thereto, the central unit 64 may be connected to any kind of biometrical sensor, such as a retina or iris scanner or a fingerprint scanner. Once the authentication session is completed, each of the surgical staff members that has performed the authentication session is added as a group member to the system. The sensing units 60A-60D track each of the group members continuously based on the information obtained during the authentication session, and the member profile available from the memory unit 71. The authentication session may use an auxiliary camera to record any non-permanent attributes of the group members, such as the color of their clothes or any other attributes that may not be the same every day. During tracking, in case any of the group members temporarily leaves the field of view of the sensor units or cameras 60A-60D, the continuous tracking of this group member is interrupted and this may require the group member to perform the identity authentication session again upon entering the field of view. As will be appreciated, in other embodiments, this may be resolved by any system that reliably enables to regain or resolve this interruption (e.g. an RFID scanner). To eliminate errors as much as possible, redoing the identity authentication session is preferred in critical situations and environments such as medical settings.

If one of the group members 39-45 performs a gesture such as to provide an instruction to the system, this is recorded by the sensor units 60A-60D during tracking, the locations of each group member may for example be tagged by the system continuously. Upon performing a gesture, due to the tagging of the person in the data (e.g. image) of the sensor unit 60A-60D, an association between the instruction and the group member providing the instruction may be immediately made by the system. This information may be provided as an event through the network 62 to the communication unit 70 in the central unit 64. The control unit 65 receives this information from the communication unit 70. The control unit 65 comprises processor 68. The control unit uses the processor to identify, upon detection of the instruction, a control command associated with the instruction provided. To do this, the detected instruction is associated with the instructing group member. Memory unit 71 is accessed for retrieving member profile data of the instructing group member therefrom, and a matching is made between the detected instructions and a reference or reference instruction in the member profile data. Once the matching is made, the intended control command to be provided to any one or more of the devices 48, 50, 52, 54, 55, 56 is identified. Since the embodiment illustrated in FIG. 3 the central unit 64 controls operation of multiple devices 48-56, using the member profile not only the intended control command is identified but also the device for which it is intended. As described hereinbefore the gestures and meaning of the gestures for each of the group members 39-45 may be personalized using the member profile data stored in the memory 71.

Although in FIG. 3 a central unit 64 comprising the control unit 65 and processor 68, the communication unit 70 and the memory unit 71 are illustrated as a single apparatus, in different embodiments one or more of these units may be implemented as a stand alone device or in combination with other such parts to cooperate such as to form the control unit.

Figure 4:
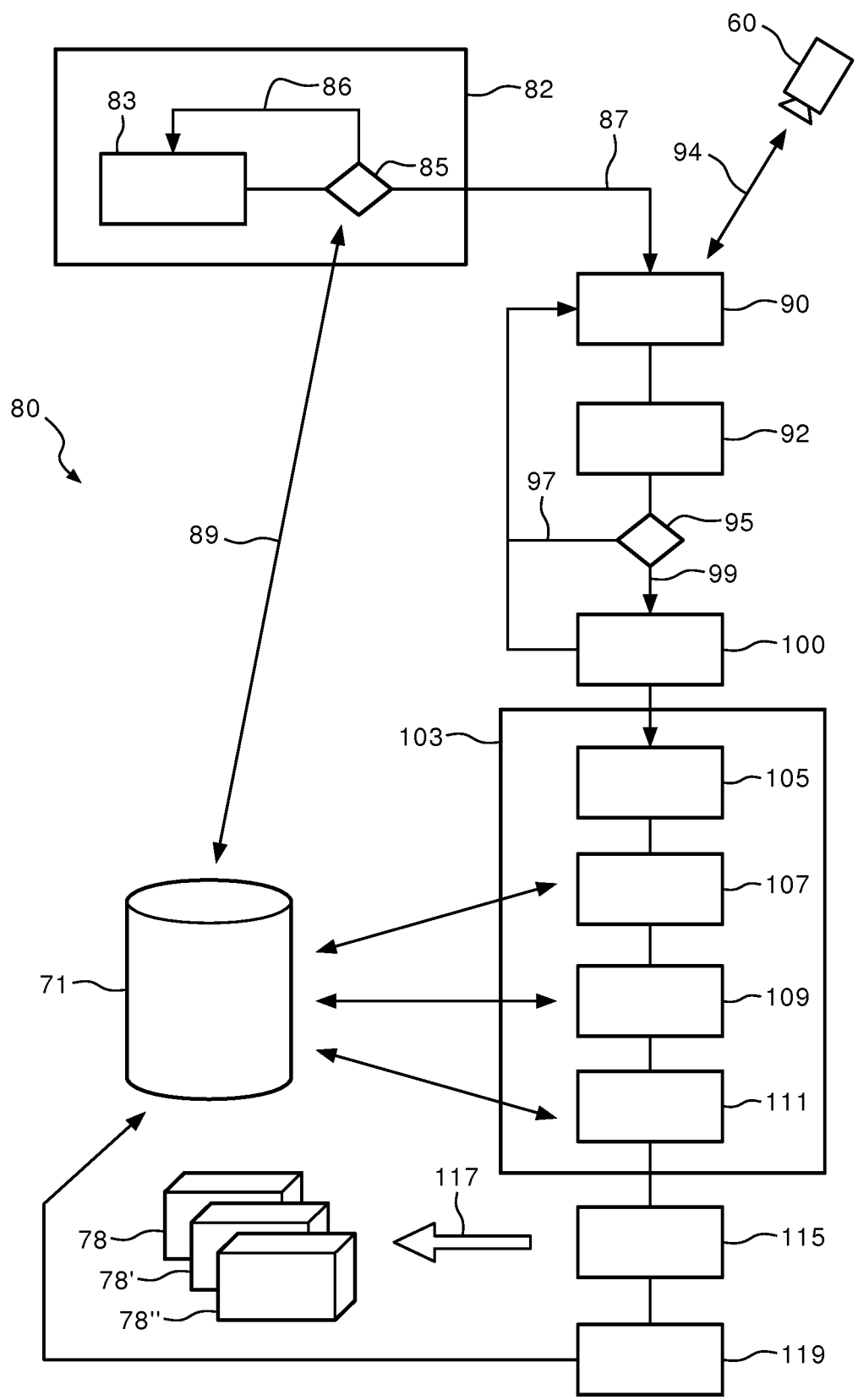
FIG. 4 schematically illustrates a method of the present invention.

A method in accordance with the present invention is further schematically illustrated in FIG. 4. FIG. 4 illustrates the memory unit 71 and the tracking system 60 generally indicated as a single device. Tracking system 60 may be comprised of a plurality of sensor units such as camera units, microphones, or any other scanners that may be applied for tracking persons. For simplicity, in FIG. 4 it is illustrated as a single device 60. FIG. 4 also illustrates a plurality of devices 78, 78'and 78" that are to be controlled using a method of the present invention.

The method may start with adding one or more group members to form a group. This is implemented using an identity authentication session 82. The authentication session 82 may be applied for all group members at the beginning of the method of the present invention. However, the skilled person may understand that the identity authentication session may be performed at any moment during the method of the present invention to add additional group members to the group. Therefore, although step 82 is illustrated at the beginning of the method, it may be appreciated that the authentication session may be applied at any other moment as well. The identity authentication session 82 is entered upon initiative of a user that desires to be added to the group as a group member.

In step 83, input is received from the user for performing the authentication. This input may be provided using a standard log-on via a log-on device such as device 76 in FIG. 3, but may also involve a biometrical scanner such as scanner 74 in FIG. 3 to perform the authentication. Once the input has been received, in step 85 the authentication session will decide whether or not the new group member can be added to the group. To perform step 85, authentication session 82 may optionally access memory unit 71 to retrieve a group profile 89, for example to check whether the user to be added as a group member is authorized to be part of this specific group applied for. For example, certain staff members may be authorized to be part of a certain team, while not being authorized to be part of other teams. Therefore, member profiles for such users may be present in a system of the present invention, however even though the member profile is present in the memory unit 71 of the system, if the group member is not part of the group profile access to the group will be denied in step 85.

In case authentication fails or in case access is denied, the authentication session, as indicated by arrow 86, returns back to step 83 waiting for input from the same or another user. In case the identity authentication session is successful, the method continues in step 87 by providing the details to the tracking systems as being one of the group members.

In step 90 after authentication, each of the group members authenticated are continuously monitored by the tracking system 60. The input received from the tracking system to this step is generally indicated by double arrow 94. Using the authentication information, the persons present in the data received from the tracking system may be continuously tagged in step 92. In step 95 it is decided whether or not one or more of the group members has provided an instruction which is detected as a gesture or sound or pose or the like by the tracking system 60. Step 100 (via branch 99) will be performed when the receipt of an instruction is successfully confirmed in step 95. Tracking (step 90) and tagging (step 92) will continuously performed while the control unit performs step 95 or any of the subsequent steps. This is to ensure that no instructions are missed. The control unit may receive instructions at any time, and when the system's resources may be temporarily busy, such instructions may for example be stacked in memory, or processed based on priority settings, or forwarded to an auxiliary unit. In FIG. 4, branch 97 indicates a continuous monitoring for instructions or actions to be processed—not a stopping of the procedure until the last instruction is processed. In step 100 the detected instruction is associated with the group member providing the instruction using the tagging which was added in step 92 and the system continues with identification in step 103 of the control command that is associated with the instruction received. In step 105 member profile data from the memory unit is accessed, and in step 107 a detected instruction is compared with reference instructions in the member profile data such as to match the detected instruction with any of the reference instructions. Once such a match is made, the control command that is associated with the matching reference instruction can be identified. Optionally, if the method is used for controlling a plurality of devices (i.e. here devices 78, 78' and 78"), in step 109 also the device for which the control command is intended can be identified using the member profile data from the memory unit 71. Therefore, as a further option in step 111, the method may also verify whether the control command that is intended to be provided by the group member to the respective device is authorized for this group member. This verification may be performed in different ways, for example the authorization can be identified using either the member profile data or the group profile data from the memory unit 71.

In step 115, the identified control command is provided to the identified device 78, 78' or 78" as indicated by arrow 117. Moreover, in step 119 the control command identified is stored in a log retained in the memory unit 71 together with for example a timestamp, the group member providing the instruction and any other data that may be of relevance. Such a log can be used for training purposes or for quality checks.

This invention proposes a system solution that is aware of (the identity of) the person controlling (a number of) complex equipment. As a consequence the interaction between the user and the system becomes a personalized two-way dialog that allows multiple users to interact with the equipment in the same time. This is achieved by tracking each individual and tagging each input he gives to the system with the individual's identity.

At any given moment more than one person in the surgical theatre could be in need of controlling part or certain features of a medical system. It is crucial to avoid giving inconsistent or conflicting commands to the system. Conventional systems are unaware of who (in other words what is the role, permissions and personal preferences of the human that) is behind a control action. By allowing a medical system to be controlled by human gestures/postures/voice it becomes important for the system to become aware of the human who is executing the control action in order to ensure the medical system behaves in a consistent and predictable way. The staff in a surgical theatre can be uniquely identified (for e.g. with retina control or fingerprint) and then continuously tracked (for e.g. with face recognition). By tracking each individual the input he gives to the system can be tagged with the identity of the issuer of the input. The system can then react adequately leading to a highly personalized dialog between user and system.

This invention proposes to first uniquely identify an individual (e.g. retina control or fingerprint) and then continuously track (face recognition, etc.) him and his commands. His gestures/postures/voice commands are analyzed by the tracking system and matched against the set of commands known for that user. A recognized command becomes an event that is tagged with his unique identity, as well as location and timestamp. An event combined with the individual's role, permissions and personal preferences (unique set of gestures per user) leads to a reaction of the system and appropriate feedback. The system might react differently to the same input depending on the identity tag attached to it. This personalized dialog can happen in parallel for multiple users of the same system. The degree of personalization by the system is flexible: users could provide their own preferred set of gestures the system should react to, or how the system should respond thereto; and users may provide their own preferred feedback mechanism. Due to the awareness the system builds about the user, a better coherence over time of the interaction between user and system can be achieved.

As an advantage of the invention, the detectability of gestures may be improved since the system may be tuned to the various gestures each user does. Moreover, the system may be adapted to users with disabilities or preferences induced by the type of work they perform (e.g. a user that cannot use his arm could have its own personalized set of commands that the system reacts to). Further, the invention can be used to personalize the way the users interact with the system, e.g. one surgeon could raise his arm to trigger a scan while another could shake his head. Also, the invention may be used build a trail of everything that happened. For example, in a surgical environment this may be used to later detect a mistake or the cause of a certain problem with a patient; while in a workflow dependent environment this kind of system helps in performing workflow analysis.

The method and system of the invention may be extended by including a further system that manages the identities and personal preferences of the users of the system. Another possible extension is for the system to be provided with context awareness derived from the dialogs of people in the room.

Although in the above description the invention has been explained and illustrated with reference to some specific embodiments thereof, the scope of the invention is merely defined by the scope of the appended claims.

The invention claimed is:

1. A method, comprising:
continuously monitoring, using one or more sensors, a plurality of authenticated members of a group to detect an instruction,
wherein the instruction is provided by an instructing authenticated member of the group,
wherein each of the authenticated members is authenticated by a user input device to provide instructions, and
wherein the instruction includes one of a visual instruction and an audible instruction;
associating, by a controller, the instruction with the instructing authenticated member;
accessing, from memory, member profile data of the instructing authenticated member which is stored in the memory, wherein the member profile data of the instructing authenticated member comprises a set of reference instructions for the instructing authenticated group member;
matching the detected instruction with a matching reference instruction selected from the set of reference instructions in the member profile data of the instructing authenticated member;
identifying a device, and a control command for controlling the device, from the matching reference instruction;
verifying, from the member profile data of the instructing authenticated member, whether the instructing authenticated member is authorized to provide the identified command to the identified device;
providing, by the controller, the identified control command to the identified device only when the detected instruction matches the matching reference instruction in the member profile data of the instructing group member and the instructing authenticated member is authorized to provide the identified control command to the identified device; and
ignoring any instructions provided any person who is not an authenticated member of the group.

2. The method of claim 1, further comprising storing the detected instruction in the memory, wherein the identified control command, and a member identifier of the instructing authenticated member are associated with the detected instruction.

3. The method of claim 1, further comprising:
authenticating, by the user input device, a user to produce an authenticated user;
accessing a group profile from the memory; and
identifying the authenticated user as an authenticated member of the group based on the profile.

4. The method of claim 1,
wherein the controller comprises a central unit,
wherein the central unit receives sensor signals from the one or more sensors, and
wherein the memory is accessible by the controller, the method further comprising:
identifying, by the controller, a candidate device for receiving the control command, wherein the candidate device is identified by the matching of the detected instruction with the matching reference instruction in the member profile data of the instructing authenticated member.

5. The method of claim 1, wherein the at least one of the one or more sensors is configured to receive at least one of visual images to detect gestures or poses, and audio signals to detect voice or sounds.

6. The method of claim 1,
wherein the one or more sensors are disposed within an operating room having a plurality of devices,
wherein the plurality of authenticated users are disposed within the operating room,
wherein the device is one of a plurality of devices disposed within the operating room, and
wherein at least a first authenticated user among the authenticated users of the group, based on the member profile data of the first authenticated user stored in the memory, is unable to access at least some functions of the devices which may be accessed by a second authenticated user among the authenticated users of the group based on the member profile data of the second authenticated user stored in the memory.

7. An apparatus, comprising:
a user input device;
one or more sensors configured to continuously monitor a plurality of authenticated members of a group to detect an instruction,
wherein the instruction is provided by an instructing authenticated member of the group,
wherein each of the authenticated members is authenticated by interacting with the user input device,
wherein the one or more sensors are configured to receive at least one of visual images and audible signals, and
wherein the instruction is one of a visual instruction and an audible instruction;
a memory configured to store member profile data for each of the authenticated members of the group, wherein the member profile data for each authenticated member of the group comprises a corresponding set of reference instructions for said authenticated member; and
a controller communicatively connected to the one or more sensors, wherein the controller is configured to receive one or more output signals from the one or more sensors, and wherein the controller includes a processor,
wherein the processor is configured to:
associate the detected instruction with the instructing authenticated member,
access the member profile data of the instructing authenticated member from the memory,
match the instruction with a matching reference instruction selected from the set of reference instructions in the member profile data of the instructing authenticated member,
identify a device, and a control command for controlling the device, from the matching reference instruction,
verify, from the member profile data of the instructing authenticated member, whether the instructing authenticated member is authorized to provide the identified command to the identified device,
provide the identified control command to the identified device only when the instruction matches the matching reference instruction in the member profile data of the instructing group member and the instructing authenticated member is authorized to provide the identified control command to the identified device; and
ignore any instructions provided any person who is not an authenticated member of the group.

8. The apparatus of claim 7, wherein the user input device comprises at least one of a biometrics scanner, including an iris or retina scanner for authenticating a user based on personal eye characteristics, or a fingerprint scanner; a keyboard for entering personal log-on details, a touch sensitive screen, and a camera.

9. The apparatus of claim 7,
wherein the one or more sensors comprise at least one imaging device and an audio sensor,
wherein the imaging device comprises one or more cameras,
wherein the one or more cameras are arranged to observe a region, and
wherein the audio sensor comprises one or more microphones for sensing audio signals.

10. The apparatus of claim 7,
wherein the one or more sensors are disposed within an operating room having a plurality of devices,
wherein the plurality of authenticated users are disposed within the operating room, wherein the device is one of a plurality of devices disposed within the operating room, and
wherein the processor is configured to deny access to at least some functions of the devices by a first authenticated user among the authenticated users of the group, based on the member profile data of the first authenticated user stored in the memory, and to permit access to the at least some functions of the devices by a second authenticated user among the authenticated users of the group, based on the member profile data of the second authenticated user stored in the memory.

11. A non-transitory computer readable storage-medium, wherein the computer readable storage-medium embodies computer instructions which, when executed by an apparatus for controlling operation of a device, configure the apparatus to:
continuously monitor, using one or more sensors of the apparatus, a plurality of authenticated members of a group to detect an instruction,
wherein the instruction is provided by an instructing authenticated member of the group,
wherein each of the authenticated members is authenticated by a user input device to provide instructions, and
wherein the instruction includes one of a visual instruction and an audible instruction;
associate, by a controller of the apparatus, the instruction with the instructing authenticated member,
access, from memory of the apparatus, member profile data of the instructing authenticated member which is stored in the memory, wherein the member profile data of the instructing authenticated member comprises a set of reference instructions for the instructing authenticated group member,
match the instruction with a matching reference instruction selected from the set of reference instructions in the member profile data of the instructing authenticated member;
identify a device, and a control command for controlling the device, from the matching reference instruction;
verify, from the member profile data of the instructing authenticated member, whether the instructing authenticated member is authorized to provide the identified command to the identified device;

provide, by the controller, the identified control command to the identified device only when the instruction matches the matching reference instruction in the member profile data of the instructing group member and the instructing authenticated member is authorized to provide the identified control command to the identified device; and ignore any instructions provided any person who is not an authenticated member of the group.

12. The computer readable storage-medium of claim 11, wherein the one or more sensors are disposed within an operating room having a plurality of devices, wherein the plurality of authenticated users are disposed within the operating room, wherein the device is one of a plurality of devices disposed within the operating room, and wherein computer instructions, when executed by the apparatus, further configure the apparatus to deny access to at least some functions of the devices by a first authenticated user among the authenticated users of the group, based on the member profile data of the first authenticated user stored in the memory, and to permit access to the at least some functions of the devices by a second authenticated user among the authenticated users of the group, based on the member profile data of the second authenticated user stored in the memory.

* * * * *